United States Patent [19]
Hill et al.

[11] Patent Number: 5,665,804
[45] Date of Patent: Sep. 9, 1997

[54] SILICONE LATEX SOLVENT THICKENING

[75] Inventors: Michael Philip Louis Hill; Eric Jude Joffre; Linda Moy Madore, all of Midland, Mich.

[73] Assignee: Dow Corning Corporation, Midland, Mich.

[21] Appl. No.: 596,853

[22] Filed: Feb. 5, 1996

[51] Int. Cl.$^6$ ............................ C08K 5/54; A61K 7/42
[52] U.S. Cl. .................... 524/268; 524/588; 524/837; 524/457; 524/863; 524/731; 424/59; 424/60; 424/63; 424/78.03; 424/407; 424/486; 424/401
[58] Field of Search .......................... 524/588, 837, 524/457, 863, 268, 731; 424/59, 60, 63, 78.03, 407, 486, 401

[56] References Cited

U.S. PATENT DOCUMENTS

| | | | |
|---|---|---|---|
| 4,743,670 | 5/1988 | Yoshida et al. | 528/15 |
| 4,980,167 | 12/1990 | Harashima et al. | 424/401 |
| 4,990,556 | 2/1991 | Shimizu et al. | 524/475 |
| 5,064,894 | 11/1991 | Desmonceau et al. | 524/503 |
| 5,089,253 | 2/1992 | Halloran | 424/47 |
| 5,092,922 | 3/1992 | Kuwata et al. | 106/3 |
| 5,266,321 | 11/1993 | Shukuzaki et al. | 424/401 |
| 5,399,342 | 3/1995 | Krzysik | 424/59 |

FOREIGN PATENT DOCUMENTS

| | | |
|---|---|---|
| 304946 | 3/1989 | European Pat. Off. . |
| 545002 | 6/1993 | European Pat. Off. . |
| 647672 | 4/1995 | European Pat. Off. . |

*Primary Examiner*—Karen A. Dean
*Attorney, Agent, or Firm*—James L. DeCesare

[57] ABSTRACT

The viscosity of a solvent is modified by thickening the solvent with a silicone latex. A silicone latex having a plurality of crosslinked polysiloxane particles is first prepared by mixing the siloxane polymer, a surfactant, and water; emulsifying the mixture to a gel phase; diluting the emulsion with water; adding a cure package (i.e., a catalyst, a crosslinker, or both, or a self catalytic crosslinker); and then without removing the water from the latex and after the particles of siloxane polymer in the latex have been cured, mixing the latex and solvent to thicken the solvent, forming viscous liquids, gels, and pastes. These latex thickened solvent compositions have beneficial properties such as clarity, shelf stability, and ease of preparation; and therefore have wide areas of application, especially as additives in antiperspirants, deodorants, and other personal care applications.

16 Claims, No Drawings

SILICONE LATEX SOLVENT THICKENING

CROSS-REFERENCE TO RELATED APPLICATIONS

This application is related to a first commonly assigned prior copending application U.S. Ser. No. 08/430,776, filed Apr. 27, 1995, entitled "Shelf Stable Cross-Linked Emulsions With Optimum Consistency And Handling Without The Use Of Thickeners". The first application describes a silicone latex and method for its preparation, which are utilized in the present application.

The present application is also related to a second commonly assigned prior copending application U.S. Ser. No. 08/430,047, filed Apr. 27, 1995, entitled "Elastomers From Silicone Emulsions Having Self Catalytic Crosslinkers". The second application also describes a silicone latex and method for its preparation, but in the second application a self catalytic crosslinker performs the crosslinking function of the crosslinker and catalyst in the first application.

BACKGROUND OF THE INVENTION

This invention is directed to aqueous crosslinked polysiloxane dispersions blended with silicone or organic fluids to produce new materials with novel properties.

Cured silicone rubber powders have been made by first preparing a water-based emulsion of a curable silicone composition, then curing the composition to form a water based dispersion of cured silicone rubber powder by heating it to 80° C. to effect crosslinking, and finally removing the water from the water-based dispersion to harvest the rubber. The disadvantage of this approach is that the initial water-based dispersion only contains about 35% silicone solids. The remaining 65% of water is removed through a spray drying process. Agglomeration occurs in the spray drying process resulting in rubber powder particle sizes larger than those occurring in the latex (the dispersion of the crosslinked rubber). So finally, a sieving procedure is carried out to remove certain particle sizes.

The advantage of our invention, in contrast, is that we have found unexpectedly, that the viscosity of a fluid can be modified with a silicone latex without removing the water from the silicone latex. This eliminates the heating, harvesting, and sieving procedures. This is possible because the silicone latex is provided as an extremely high internal phase ratio latex, that is, it contains a crosslinked or cured rubber phase up to 95%, with the remainder being the water continuous phase. It is quite unexpected that one could swell the individual silicone latex particles with a solvent in the presence of a water continuous phase.

This particular silicone latex represents several significant advances in the art. First, the process of making the dispersion is improved since the high solids gel phase provides for a higher shear and lower particle size distribution. Second, an advantage is that due to the high polymer solids content of the diluted gel (above 75%), the composition does not require thickeners or other rheology modifiers to achieve excellent handling characteristics. A third advantage is the versatility of the process, allowing mixing of silicone polymer, water, surfactant, and cure package (i.e., a catalyst, a crosslinker, or both, or a self catalytic crosslinker), in the manufacture of a high solids oil-in-water emulsion as a gel phase intermediate. The gel phase intermediate can be used immediately after preparation or stored. The high solids gel is then diluted with water to form a dispersion having greater than 75% silicone solids content. The gel can be further processed by adding additional ingredients, if desired, and diluting the dispersion to the desired solids content.

BRIEF SUMMARY OF THE INVENTION

The invention relates to a method of modifying the viscosity of a solvent by thickening the solvent with a silicone latex which has a plurality of crosslinked polysiloxane particles. The silicone latex is prepared by (A) forming a mixture containing a siloxane polymer, a surfactant, and water; (B) emulsifying the mixture into a gel phase; (C) diluting the emulsion with further water; and (D) adding a cure package.

The cure package can be a catalyst or a crosslinker, or both, or a self catalytic crosslinker. Then, without removing the water from the latex, and after the particles of siloxane polymer in the latex have been cured, mixing the latex and the solvent together to thicken the solvent to a desired viscosity or form viscous liquids, gels or pastes.

The invention also relates to silicone latex solvent thickened compositions prepared according to the above method, which compositions have a variety of uses in the personal care arena, as well as other areas of application. The silicone latex provides a means to modify the rheology of various fluids which enhances formulating capability, and it can function as a reservoir for various fluids and solvents.

These and other features and objects of our invention will become apparent from a consideration of the detailed description.

DETAILED DESCRIPTION

In preparing our latex thickened solvent compositions, we make use of silicone latexes and methods of producing same described in the two copending applications U.S. Ser. No. 08/430,776, filed Apr. 27, 1995, and U.S. Ser. No. 08/430,047, filed Apr. 27, 1995, both considered incorporated herein by reference. The silicone latex is free of rheology modifiers, contains a plurality of crosslinked polysiloxane particles, and has at least 75% silicone content by weight. It is an aqueous dispersion of crosslinked polysiloxane capable of crosslinking via condensation, addition, or free radical reactions. The latex is prepared by combining:

(i) 100 weight parts of a siloxane polymer or polymer mixture having a viscosity of greater than 5,000 mPa.s (5,000 centistokes) but less than 500,000 mPa.s (500,000 centistokes) at 25° C., the siloxane polymer or polymer mixture having at least one polymer species of the formula:

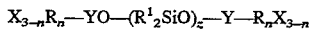

where n is 0, 1, 2 or 3; z is an integer from 500–5,000; X is hydrogen, a vinyl group, a hydroxyl group, any condensable, or hydrolyzable group; Y is a silicon atom, $\equiv Si-(CH_2)_m-SiR^1_2-$ group, or $\equiv Si-(CH_2)_m-SiR^1_2OSiR^1_2(CH_2)m-SiR^1_2-$ group, where m is 1–8; R is individually selected from aliphatic alkyl, aminoalkyl, polyaminoalkyl, epoxyalkyl, alkenyl, or aromatic groups; and $R^1$ is individually selected from X, aliphatic alkyl, alkenyl, and aromatic groups, (ii) 0.5–10 weight parts surfactant, (iii) 0.5–25 weight parts water, (iv) 0.1–20 weight parts crosslinker, (v) 0.00001–20 weight parts catalyst, or (vi) 1–5 weight parts of a self catalytic crosslinker in place of crosslinker (iv) and catalyst (v).

Examples of condensable or hydrolyzable groups appropriate for X are halogen, alkoxy, amino, ketoxime, ureido, carboxyl, sulfate, sulfate ester, cyano, isocyanate, phosphate, and phosphate ester.

The aqueous dispersion is produced by mixing the silicone polymer, surfactant, and water, under sufficient shear and for a sufficient period of time to obtain a high solids "oil-in-water" emulsion, capable of forming a characteristic gel phase having at least 90% polymer solids content and having particle sizes between 0.1–20 micrometers (microns). The cure package (i.e., a catalyst, a crosslinker, or both, or a self catalytic crosslinker), may be added directly to the high solids gel phase or after dilution of the gel with water to the desired solids content. Alternatively, the cure package may be added to the mixture prior to the emulsification into the gel phase. In any case, it is important that a high solids gel is formed first after the emulsification step, and prior to dilution of the emulsion with further water. The high solids emulsion containing silicone polymer, water, surfactant, and cure package is shelf-stable and may be stored as an intermediate.

The surfactant can be a nonionic surfactant, cationic surfactant, anionic surfactant, amphoteric surfactant, or a mixture thereof. The surfactant is present in the composition in an amount of 0.5–10 parts by weight based on 100 parts by weight of siloxane polymer, preferably 2–10 parts by weight.

Most preferred are nonionic surfactants such as polyoxyalkylene alkyl ethers, polyoxyalkylene sorbitan esters, polyoxyalkylene esters, polyoxyalkylene alkylphenyl ethers, ethoxylated amides, ethoxylated siloxanes, and block copolymers of propylene oxide and ethylene oxide. Some representative nonionic surfactants commercially available and useful in our invention are TERGITOL® TMN-6, TERGITOL® 15S40, TERGITOL® 15S3, TERGITOL® 15S5, and TERGITOL® 15S7 produced by Union Carbide Corporation (Danbury, Conn.); BRIJ 30 and BRIJ 35 produced by ICI CHEMICALS (Wilmington, Del.); TRITON® X405 produced by ROHM AND HAAS (Philadelphia, Penn.); MAKON 10 produced by STEPAN Company (Northfield, Ill.); ETHOMID O/17 produced by AKZO Inc. (Chicago, Ill.); and PLURONIC® F38 produced by BASF Corporation (Parsippany, N.J.).

Some additional nonionic surfactants commercially available and useful in our invention are ALKAMULS PSML-20, a product and tradename of Rhone-Poulenc (New Jersey), Surfactant & Specialty Division, Cranberry, N.J., for polyoxyethylene sorbitan (20) monolaurate; ALKAMULS PSMO-20, a product and tradename of Rhone-Poulenc (New Jersey), Surfactant & Specialty Division, Cranberry, N.J., for polyoxyethylene sorbitan (20) monooleate; RENEX 36, a product and tradename of ICI Surfactants, Wilmington, Del., for ethoxylated tridecyl ether; and GENAPOL® UD, a product and trademark of Hoechst Celanese Corporation, Specialty Chemical Group, Charlotte, N.C., for ethoxylated undecyl alcohol.

Reference may be had to the copending applications for the various types of cationic surfactants, anionic surfactants, and amphoteric surfactants which can be used. However, some representative examples of commercial surfactant products follows.

Thus, appropriate cationic surfactants include ARQUAD T27W, ARQUAD 16-29, ARQUAD C-33, ARQUAD T50, and ETHOQUAD T/13 ACETATE, all manufactured by AKZO CHEMIE (Chicago, Ill.); and MACKALENE 216 a product of The Mcintyre Group, Ltd., University Park, Ill.

Anionic surfactants include POLYSTEP A4, A7, A11, A15, A15-30K, A16, A16-22, A18, A13, A17, B1, B3, B5, B11, B12, B19, B20, B22, B23, B24, B-25, B27, B29, and POLYSTEP C-OP3S; ALPHA-STEP ML40, and ALPHA-STEP MC48; STEPANOL MG; and BIO-TERGE AS-40, all produced by STEPAN Company (Northfield, Ill.), HOSTAPUR SAS produced by HOECHST CELANESE (Chatham, N.J.); HAMPOSYL C30 and HAMPOSYL L30 produced by W.R.GRACE & CO. (Lexington, Mass.); and MIRANATE® LEC, a trademark and product of Rhone-Poulenc (New Jersey), Surfactant & Specialty Division, Cranberry, N.J. Its INCI CTFA name is SODIUM LAURETH-13 CARBOXYLATE.

Amphoteric surfactants include REWOTERIC AM TEG, REWOTERIC AM DLM-35, REWOTERIC AM B14 LS, REWOTERIC AM CAS, and REWOTERIC AM LP, all produced by SHEREX CHEMICAL CO. (Dublin, Ohio); and SCHERCOTAINE SCAB a product of Scher Chemicals, Inc., Clifton, N.J.

In addition to adding the surfactant to the polysiloxane, the dispersion also includes a predetermined amount of water. The water is present in the composition in an amount of 0.5–25 parts by weight based on 100 parts by weight of siloxane polymer, preferably 6–15 parts by weight.

After the mixture of siloxane polymer, surfactant, and water is formed, the mixture is emulsified by mixing with sufficient shear, and for a sufficient period of time to form a high solids gel phase. Either crosslinker or catalyst, or both, or the self catalytic crosslinker, (i.e., the cure package) may be added to the mixture prior to or after emulsification. The mixing will preferably take place at a temperature of 10°–70° C. If the cure package is added after the emulsification step, it may be added either prior or after diluting the gel phase with water to the desired solids content. The gel phase should have a polymer solids content of at least 90%, preferably 90–96%. The polymer solids content in the gel phase can be as high 96–98% polymer.

Any type of mixing equipment may be used to perform the emulsification step, such as batch mixers, planetary mixers, continuous compounders such as single or multiple screw extruders, dynamic or static mixers, colloid mills, homogenizers, and sonolators, or combinations thereof.

The high solids (90%) gel phase formed by emulsifying siloxane polymer, surfactant, and water, is shelf-stable and capable of being stored for as many as 24 months prior to further processing.

After emulsification, the gel phase may be diluted with water to achieve a silicone solids content of greater than 75%. Generally, amounts in the range of 5–30 parts by weight is added to achieve a solids content in the range of 75–98%. A more preferred solids range is 80–92% and the most preferred range is 84–90%. The high silicone solids content of the final dispersion is critical and distinguishes this latex over compositions in the prior art.

The amount and type of crosslinker and catalyst used depends on the type of silicon cure system employed to cure the composition. In general, the amount of crosslinker will be 0.1–20 parts by weight per 100 parts by weight of siloxane polymer, preferably 0.1–10 parts by weight. The amount of catalyst, will be 0.00001–20 parts by weight per 100 parts by weight of siloxane polymer, preferably 0.00001–10 parts by weight. Condensation systems may require larger amounts of catalyst, while addition systems may require lesser amounts. The crosslinker or catalyst may be added either individually before or after emulsification, or both may be added before or after emulsification.

One class of silicon cure systems appropriate to our invention involves condensation reactions, for instance, between silanol ($\equiv$Si—OH) and silicon hydride ($\equiv$Si—H) groups; between silanol ($\equiv$Si—OH) and hydrolyzable or condensable silyl groups such as ≡Si—OC(O)CH$_3$, ≡Si—NR$_2$, and ≡Si—ON═CR$_2$; between silicon hydride and hydrolyzable or condensable groups; and between two hydrolyzable or condensable groups of the same or different species.

One example of this cure system is the reaction between a siloxane polymer bearing silanol groups and a crosslinking compound bearing hydrolyzable groups directly attached to silicon atom(s). Another example of this cure system is the reaction between a siloxane polymer bearing hydrolyzable or condensable groups directly attached to silicon atom(s) and a crosslinking compound bearing silanol groups. Yet another example of this cure system is the reaction between two siloxane polymers bearing hydrolyzable or condensable groups attached directly to silicon atom(s). A further example of this cure system is the reaction between a siloxane polymer bearing hydrolyzable or condensable groups directly attached to silicon atom(s) and a siloxane polymer bearing active hydrogen atoms such as hydroxyl, ureido, mercapto, or amino groups.

Catalysts for these condensation cure chemistries effect the reaction between polymer and crosslinking compound, and include organometallic compounds, amino compounds, carboxylic acids, salts of amino compounds with carboxylic acids or other acids, low molecular weight polyamide resins obtained by the reaction of excess polyamines with polybasic acids, the reaction products between epoxy compounds and an excess of polyamines, and noble metal compounds.

Typically, the crosslinking compound is a silane, a siloxane oligomer, a siloxane polymer, a siloxane resin, a silicon-modified organic oligomer, a silicon-modified organic polymer, or a silicon-modified organic resin, each bearing a hydrolyzable or condensable group attached directly to a silicon atom.

Reference may be had to the first copending application for the details of these condensation cure systems, as well as to details of the polysiloxane dispersions capable of crosslinking via free radical reactions, non-volatile cure systems, and other miscellaneous organic cure systems.

The class of silicon cure systems most preferred according to our invention, involves addition (hydrosilylation) reactions between a silicon hydride (≡Si—H) group and an alkenyl group (—(CH$_2$)$_n$—CH═CH$_2$) group. The silicon hydride group may be attached either to the polymer or the crosslinker. The alkenyl group may be attached either to the polymer or the crosslinker. If the alkenyl group is attached to the crosslinker, the crosslinker may be organic, silicon modified organic, or siloxane in nature.

The number of reactive radicals on the polymer and the crosslinker determine whether a cured elastomer is obtained. An elastomeric network is being formed by the addition cure, if the sum of the reactive radicals on the polymer and the reactive radicals on the crosslinker is at least five. For example, if the polymer has two alkenyl groups and the crosslinker has three silicon hydride groups an elastomer is obtained.

The addition cure chemistry requires a catalyst to effect the reaction between polymer and crosslinking compound. Examples of suitable catalysts preferably employed in the addition reaction are Group VIII transition metal (noble metal) compounds. Such noble metal catalysts are described in U.S. Pat. No. 3,923,705, which is incorporated by reference to show platinum catalysts. A preferred platinum compound as catalyst is the reaction product of chloroplatinic acid and an organosilicon compound containing terminal aliphatic unsaturation. It is described in U.S. Pat. No. 3,419,593, which is also incorporated by reference. When noble metal catalysts are used, they are added in an amount from 0.00001–0.5 parts per 100 weight parts of the siloxane polymer, preferably 0.00001–0.02 parts, most preferably 0.00001–0.002 parts.

In one addition cure system useful to the invention, the siloxane polymer bearing alkenyl groups is reacted with a crosslinker, having on average at least two silicon-bonded hydrogen atoms per molecule. The reaction occurs in the presence of a hydrosilylation catalyst. The siloxane polymer contains at least one alkenyl group. However, in order to obtain sufficient curability, the siloxane polymer should contain at least 1.1, preferably from 1.5–4 reactive alkenyl groups.

The silicon hydride crosslinker can be a hydrolyzable silicon hydride, a polymeric or oligomeric compound containing on average at least two hydrogen-silicon bonds such as a polyorganohydrogen siloxane, an alkylhydrogen cyclosiloxane, or a liquid copolymer containing SiO$_2$ and/or RSiO$_{3/2}$ units and bearing silicon-bonded hydrogen radicals. The silicon hydride crosslinker can also be an organic polymer or resin bearing ≡Si—H groups, or a silsesquioxane containing hydrogen.

Examples of crosslinkers are trimethylsilyl endblocked polymethylhydrogen siloxane and methylhydrogen cyclosiloxane. The ≡SiH functional crosslinker is added in sufficient amount to provide at least one hydrogen atom for each vinyl group in the polydiorganosiloxane polymer. In a typical preparation, the catalyst would be present in the composition in an amount of from 0.00001–0.5 parts, and silicon hydride crosslinker in an amount of from 0.1–10 parts, each by weight, of siloxane polymer.

As previously noted, U.S. Ser. No. 08/430,047, filed Apr. 27, 1995, relates to a self catalytic crosslinker to perform the crosslinking function of separate catalysts and crosslinkers. In this optional mode, at least one self catalytic crosslinker is present in the composition. The term "self catalytic crosslinker" means a molecule that has at least one leaving group as the catalytic species. While in certain circumstances only one self catalytic crosslinker may be needed to produce an elastomer having the desired physical properties, two or more self catalytic crosslinkers may be added to the reaction mixture. In addition, the self catalytic crosslinker or crosslinkers may be added with a conventional catalyst. However, adding the self catalytic crosslinker with a conventional catalyst is not required, and the compositions may in fact be free of conventional catalysts. The self catalytic crosslinkers are present in an amount of 1–5 parts of total self catalytic crosslinker per 100 parts by weight of siloxane polymer.

Some typical self catalytic crosslinkers include tri- or tetra- functional compounds such as R—Si—(Q)$_3$ or Si—(Q)$_4$, where Q is carboxylic, —OC(O)R e.g. acetoxy and R is an alkyl or alkenyl group of 1–8 carbon atoms, preferably methyl, ethyl or vinyl. Other preferred Q groups hydroxyl amines —ON(R)$_2$, where R is the same or different alkyl group of 1–8 carbon atoms, e.g., —ON(CH$_2$CH$_3$)$_2$. Q may also be an oxime group such as —O—N═C(R)$_2$ where R is the same or different alkyl group of 1–8 carbon atoms, e.g., —O—N═C(CH$_3$)(CH$_2$CH$_3$). Further, Q may be an amine group such as —N(R)$_2$ where R is the same or different alkyl group of 1–8 carbon atoms or a cyclic alkyl group, e.g., —N(CH$_3$)$_2$ or —NH(cyclohexyl). Finally, Q may be an acetamido group —NRC(O)R where R is the same or different alkyl group of 1–8 carbon atoms, e.g. —N(CH$_3$)C(O)CH$_3$.

In addition, partial hydrolysis products of the aforementioned compounds may also function as self catalytic crosslinkers. This would include dimers, trimers, and tetramers, for example compounds of the formula:

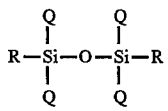

where Q and R are as defined above.

Also useful as self catalytic crosslinkers are polymeric or copolymeric species containing 3 or more Q sites located at either pendant or terminal positions or both on the backbone of a polydiorganosiloxane molecule. Examples of the pendant group include compositions of the formula:

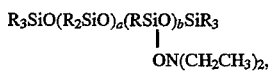

where R is the same or different alkyl group of 1–8 carbon atoms, a is zero or a positive integer, and b is an integer greater than two. In general polymeric compositions having either pendant or terminal Q groups may be used, in particular compounds of the formula $Q_{3-n}R_nSiO(R_2SiO)_zSiR_nQ_{3-n}$ where n is 0, 1, 2, or 3; z is a positive integer; R is Q or independently the same or different alkyl chain of 1–8 carbon atoms, as long as there are at least three Q groups in the molecule; and Q is as earlier defined.

Effective self catalytic crosslinkers are compounds which form tack free elastomers when mixed with functional silicone polymers in the absence of additional catalysts such as tin carboxylates or amines. In the self catalytic crosslinkers, the acetoxy, oxime, hydroxyl amine (aminoxy), acetamide, and amide groups catalyze the formation of ≡Si—O—Si≡ bonds in reactions contemplated herein.

In order to prepare compositions thickened with the silicone latex, the latex is mixed with a solvent. The silicone latex may be used to thicken a single solvent or a mixture of solvents. The term solvent as used herein is intended to mean (i) organic compounds, (ii) compounds containing a silicon atom, (iii) mixtures of organic compounds, (iv) mixtures of compounds containing a silicon atom, or (v) mixtures of organic compounds and compounds containing a silicon atom; that are used on an industrial scale to dissolve, suspend, or change the physical properties of other materials. In general, the organic compounds are aromatic hydrocarbons, aliphatic hydrocarbons, alcohols, aldehydes, ketones, amines, esters, ethers, glycols, glycol ethers, alkyl halides, or aromatic halides.

Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; fatty oils such as corn oil, soybean oil, olive oil, rape seed oil, cotton seed oil, sardine oil, herring oil, and whale oil; and "other" miscellaneous types of organic solvents such as acetonitrile, nitromethane, dimethylformamide, propylene oxide, trioctyl phosphate, butyrolactone, furfural, pine oil, turpentine, and m-creosol.

Representative of solvents containing a silicon atom are organic polysiloxanes having a viscosity in the range of 5–10,000 centistokes. Such polysiloxanes have repeating units

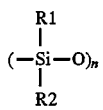

wherein n is an integer having a value greater than 1; R1 is an alkyl radical containing 1–20 carbon atoms, or a phenyl group; R2 is hydrogen, an alkyl radical containing 1–20 carbon atoms, or a phenyl group. Illustrative polysiloxanes encompassed by the above formula are polydimethylsiloxane, polydiethylsiloxane, polymethylethylsiloxane, polymethylphenylsiloxane, polydiphenylsiloxanes, diphenylsilanediol, and copolymers thereof.

Functional polysiloxanes can also be used, representative of which are acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, hexenyl functional siloxane fluids, hydrido functional siloxanes, ketal functional siloxane fluids, mercapto functional siloxane fluids, methacrylate functional siloxane fluids, methyl ester functional siloxane fluids, perfluoro functional siloxane fluids, silanol functional siloxanes, vinyl functional siloxanes, and vinylcyclohexenyl siloxane fluids.

Another particularly useful silicone solvent is a volatile methyl siloxane (VMS), which is a low viscosity silicone fluid corresponding to the average unit formula $(CH_3)_aSiO_{(4-a)/2}$ in which a has an average value of two to three. The fluid contains siloxane units joined by ≡Si—O—Si≡ bonds. Representative units are monofunctional "M" units $(CH_3)_3SiO_{1/2}$ and difunctional "D" units $(CH_3)_2SiO_{2/2}$. The presence of trifunctional "T" units $CH_3SiO_{3/2}$ results in the formation of branched cyclic volatile methyl siloxanes. The presence of tetrafunctional "Q" units $SiO_{4/2}$ results in the formation of branched linear volatile methyl siloxanes.

Linear VMS have the formula $(CH_3)_3SiO\{(CH_3)_2SiO\}_xSi(CH_3)_3$, and cyclic VMS have the formula $\{(CH_3)_2SiO\}_y$, in which x is 0–5, and y is 3–6. Preferably, the volatile methyl siloxane has a boiling point less than 250° C. and a viscosity of 0.65–5.0 centistokes (mm²/s). Some representative volatile methyl siloxanes are:

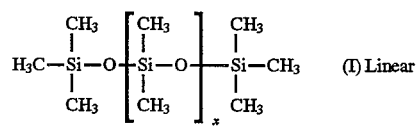

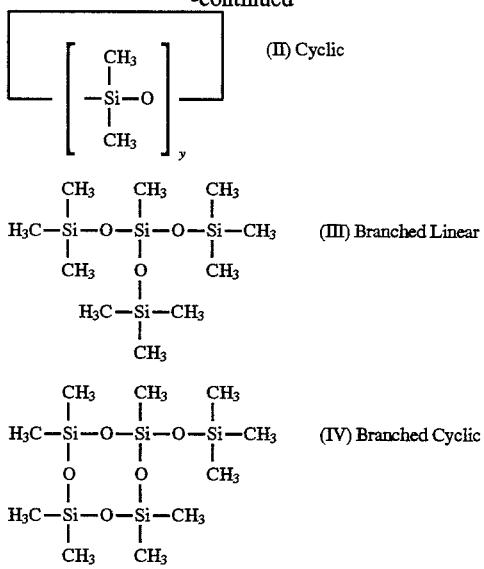

Cyclic volatile methyl siloxanes (II) have been assigned the International Nomenclature Cosmetic Ingredient (INCI) name "CYCLOMETHICONE" by The Cosmetics, Toiletries and Fragrance Association, Inc., (CTFA) Washington, D.C. Cyclic and linear methyl siloxanes are clear fluids, essentially odorless, non-toxic, non-greasy, non-stinging, and non-irritating to skin.

VMS leave substantially no residue after thirty minutes at room temperature (20°–25° C./68°–77° F.) when one gram is placed at the center of No. 1 circular filter paper of 185 millimeters diameter, supported at its perimeter in open room atmosphere. Volatile methyl siloxanes may be used alone or mixed together. Mixtures result in solutions having evaporating behaviors different from individual fluids.

Representative linear volatile methyl siloxanes (I) are hexamethyldisiloxane (MM) with a boiling point of 100° C., viscosity of 0.65 mm²/s and formula Me₃SiOSiMe₃; octamethyltrisiloxane (MDM) with a boiling point of 152° C., viscosity of 1.04 mm²/s and formula Me₃SiOMe₂SiOSiMe₃; decamethyltetrasiloxane (MD₂M) with a boiling point of 194° C., viscosity of 1.53 mm²/s and formula Me₃SiO(Me₂SiO)₂SiMe₃; dodecamethylpentasiloxane (MD₃M) with a boiling point of 229° C., viscosity of 2.06 mm²/s and formula Me₃SiO(Me₂SiO)₃SiMe₃; tetradecamethylhexasiloxane (MD₄M) with a boiling point of 245° C., viscosity of 2.63 mm²/s and formula Me₃SiO(Me₂SiO)₄SiMe₃; and hexadecamethylheptasiloxane (MD₅M) with a boiling point of 270° C., viscosity of 3.24 mm²/s and formula Me₃SiO(Me₂SiO)₅SiMe₃.

Representative cyclic volatile methyl siloxanes (II) are hexamethylcyclotrisiloxane (D₃) a solid with a boiling point of 134° C. and formula {(Me₂)SiO}₃; octamethylcyclotetrasiloxane (D₄) with a boiling point of 176° C., viscosity of 2.3 mm²/s, and formula {(Me₂)SiO}₄; decamethylcyclopentasiloxane (D₅) with a boiling point of 210° C., viscosity of 3.87 mm²/s, and formula {(Me₂)SiO}₅; and dodecamethylcyclohexasiloxane (D₆) with a boiling point of 245° C., viscosity of 6.62 mm²/s, and formula {(Me₂)SiO}₆.

Representative branched volatile methyl siloxanes (III) and (IV) are heptamethyl-3-{(trimethylsilyl)oxy}trisiloxane (M₃T) with a boiling point of 192° C., viscosity of 1.57 mm²/s, and formula C₁₀H₃₀O₃Si₄; hexamethyl-3,3,bis{(trimethylsilyl)oxy} trisiloxane (M₄Q) with a boiling point of 222° C., viscosity of 2.86 mm²/s, and formula C₁₂H₃₆O₄Si₅; and pentamethyl {(trimethylsilyl)oxy} cyclotrisiloxane (MD₃) with the formula C₈H₂₄O₄Si₄.

One preferred VMS is octamethylcyclotetrasiloxane [(CH₃)₂SiO]₄. It has a viscosity of 2.3 centistokes (mm²/s) at 25° C., and is referred to as "D₄" since it contains four difunctional "D" units (CH₃)₂SiO₂/₂ shown as:

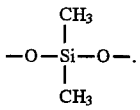

Four "D" units combine to form octamethylcyclotetrasiloxane shown in either formula below:

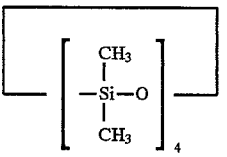

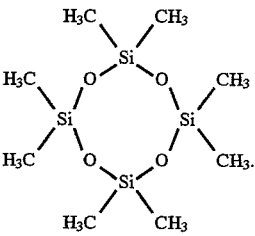

In the literature, D₄ is often called CYCLOMETHICONE or TETRAMER. It has a higher viscosity (2.3 centistokes) and is thicker than water (1.0 centistokes), yet D₄ needs 94% less heat to evaporate than water.

Another preferred VMS is decamethylcyclopentasiloxane (D5) often referred to as PENTAMER. It is shown structurally below:

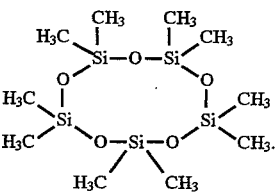

A benefit offered by using these VMS compounds as solvent is that they are a replacement for many chemicals restricted by local, state, federal, and international regulations. Thus, the Environmental Protection Agency (EPA) determined that volatile methyl siloxanes such as octamethylcyclotetrasiloxane, decamethylcyclopentasiloxane, dodecamethylcyclohexasiloxane, hexamethyldisiloxane, octamethyltrisiloxane, and decamethyltetrasiloxane, are acceptable substitutes for the CFC-113 chlorofluorocarbon (C₂Cl₃F₃) and methylchloroform (MCF). This determination is limited to cleaning in closed systems for metal cleaning, electronic cleaning, and precision cleaning, under the EPA's Significant New Alternatives Policy (SNAP).

In addition, the EPA excluded VMS as a volatile organic compound (VOC), and added VMS to a list of compounds in 40 CFR 51.100(s) excluded from the definition of VOC, on the basis that VMS compounds have negligible contribution to tropospheric ozone formation. They noted that exempting VMS from regulation as an ozone precursor contributes to achievement of important environmental goals, in that VMS might be used as a substitute for compounds listed as hazardous air pollutants (HAP).

Our thickened solvent compositions have particular value in the personal care arena. Because of volatility characteristics of the solvent component, the thickened solvent compositions can be used alone, or blended with other cosmetic fluids, to form a variety of over-the-counter personal care products.

Thus, it is useful as a carrier in antiperspirants, deodorants, and other personal care applications, since it leaves a dry feel, and does not cool the skin upon evaporation. It is lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats, to enhance gloss and drying time, and provide conditioning benefits.

In cosmetics, it will function as a leveling and spreading agent for pigments in make-ups, color cosmetics, foundations, blushes, lipsticks, eyeliners, mascaras, oil removers, color cosmetic removers, and powders. It is useful as a delivery system for oil and water soluble substances such as vitamins. When incorporated into sticks, gels, lotions, aerosols, and roll-ons, our thickened solvent composition imparts a dry, silky-smooth, pay-out.

In addition, our thickened solvent compositions exhibit other beneficial properties such as (i) clarity, (ii) the ability to combine properties of water and oil in a single phase, (iii) shelf stability, and (iv) ease of preparation; making them especially useful in antiperspirants and deodorants, in perfumes as a carrier, and for hair conditioning.

These silicone latex thickened solvent compositions have uses beyond the personal care arena, including their use as a filler or insulation material for electrical cable, a soil or water barrier for in-ground stabilization, or as a replacement for epoxy materials used in coil-on-plug designs in the electronics industry.

They are useful as carrier for crosslinked silicone rubber particles, (i) allowing ease of incorporation of the particles into such silicone or organic phases as sealants, paints, coatings, greases, adhesives, antifoams, and potting compounds, and (ii) for modifying rheological, physical, or energy absorbing properties of such phases in either their neat of finished condition.

In addition, the silicone latex thickened solvent compositions are capable of functioning as a carrier for pharmaceuticals, biocides, herbicides, pesticides, and other biologically active substances; and can be used to incorporate water and water-soluble substances into hydrophobic systems. Examples of some water-soluble substances are salicylic acid, glycerol, enzymes, and glycolic acid.

Silicone latex solvent thickened compositions according to our invention can contain 1–99 percent by weight of the silicone latex and 1–99 percent by weight of the solvent. Preferably, however, the silicone latex solvent thickened compositions contain 5–40 percent by weight of the silicone latex and 60–95 percent by weight of the solvent. Most preferably, the silicone latex solvent thickened compositions contain 5–30 percent by weight of the silicone latex and 70–95 percent by weight of the solvent. The types of silicone latex solvent thickened compositions which can be prepared range from viscous fluids, to gels, to pastes, depending upon the relative amounts of silicone latex and solvent used in their preparation.

The following examples illustrate the use of the silicone latex described above to thicken a solvent. In these examples, the silicone latex is used without removing water from the latex. In addition, the solvent to be thickened is added to the silicone latex after the particles of silicone polymer in the latex have been cured.

EXAMPLE I

Vinyl polymer/Vinyl Gum Blend Preparation 750 g of pendant vinyl containing gum consisting of 97% dimethyl, methylvinyl siloxane, dimethylvinylsiloxy-terminated copolymer [0.19% Vi, 14,240 eq wt/Vi, degree of polymerization (DP) of 9436] were mixed with 4250 g of a vinyl-endblocked siloxane fluid (450 cst, 0.46% Vi, 5853 eq wt/Vi, DP of 149) in a 10L TURELLO mixer until a homogenous viscous blend was obtained.

EXAMPLE II

Preparation of Crosslinked Latex

To the 5000 g blend prepared in Example I, 102.5 g of $Me_3SiO(Me_2SiO)_3(MeHSiO)_5SiMe_3$ were mixed together. To this blend 333.75 g of a 45% solution of Tergitol® TMN-6, an ethoxylated trimethylnonanol nonionic surfactant, were added. This material was mixed in a 10L TURELLO mixer until a very high solids oil in water emulsion was formed. 215 g of deionized water was added to dilute the emulsion to a 90% silicone solids emulsion. The average particle size of the emulsion particles was 732±449 nm as measured by a NICOMP particle size analyzer. The emulsion particles were crosslinked by the addition of 12.5 g of a platinum containing complex of 92% dimethylvinylsiloxy-terminated dimethylsiloxane, 7% tetramethyldivinyldisiloxane, and 1% 1,3-diethenyl-1,1,3,3-tetramethyldisiloxane complex. The Pt level in this mixture was about 0.5% by weight.

EXAMPLE III

Addition of Cyclic Siloxanes to the Latex

Using a HAUSCHILD laboratory centrifugal mixer, the latex prepared in Example III, and a 2.6 centistokes silicone fluid containing a mixture of 77% octamethylcyclotetrasiloxane (D4) and 23% decamethylcyclopentasiloxane (D5), were mixed together until homogenous, by incrementally adding the D4 and D5 mixture to the latex without removing water from the latex, followed by mixing. Table I shows the results of these runs.

TABLE I

| Run No. | Wt. % Cyclics | Latex gm | Cyclics gm | No. of Increm | Cyclics Increm | Mix Time Seconds | Results |
|---|---|---|---|---|---|---|---|
| 1 | 50 | 20 | 20 | 4 | 5 | 104 | gel |
| 2 | 76.7 | 10 | 32.9 | 4 | 5 | 104 | gel |
| 3 | 84.8 | 5 | 28 | 4 | 7 | 104 | liquid |

EXAMPLE IV

Addition of a Linear Siloxane to the Latex

Using the same latex prepared in Example II and without removing water from the latex, 8.14 g of the latex was mixed in a HAUSCHILD laboratory centrifugal mixer with 8.61 g of a 500 centistokes trimethylsilyl endblocked linear polydimethylsiloxane fluid. A thick gel resulted at this fluid level of 51%. An additional 8.72 g of the same siloxane fluid were added to the mixture, and a less viscous gel was observed at this increased fluid level of 68%.

EXAMPLE V

Latex Made From a High Viscosity Vinyl Endblocked Polymer and Blending of the Latex with Cyclic Siloxanes In a WHIP-MIX laboratory mixer 40 g of a vinyl endblocked polydimethylsiloxane (PDMS) (55,000 cst, 0.88% Vi, 30,810 eq wt/Vi, DP of 830), and 0.17 g of the ≡Si—H fluid described in Example II were mixed together. 2.67 g of the 45% Tergitol® TMN-6 solution used in Example II was added. The material was mixed until a high solids emulsion was obtained, and then diluted to 90% silicone solids. 0.1 g of the same platinum complex used in Example II was added to crosslink the emulsion particles. To 10 g of this latex, and without removing water from the latex, 32.9 g of the same D4 and D5 mixture used in Example III were incrementally mixed into the latex using the HAUSCHILD mixer. The total mixing time was 156 seconds. The material formed a thick gel at this fluid level of 76.7%.

These examples demonstrate that thickened solvent compositions can be prepared from blends of a 90% silicone solids latex and varying amounts of octamethylcyclotetrasiloxane, decamethylcyclotetrasiloxane, and linear siloxanes. Depending upon the solvent to silicone latex ratio, viscous fluids, gels, or pastes can be formed. By using as little as 20% silicone latex solids, one can prepare gels or paste-like materials. Viscous fluids can be prepared at lower silicone latex solids levels.

The following examples illustrate variations of our method for preparing latex thickened solvent compositions, and the use of other types of surfactants or solvent.

EXAMPLE VI

Cationic Surfactant

In a laboratory WHIP MIX mixer, 125 g of the vinyl endblocked PDMS in Example V, and 0.54 g of the ≡Si—H fluid in Example II, were mixed together. To this mixture, 10.42 g of a 40% aqueous solution of the cationic surfactant MACKALENE 216 was added. MACKALENE 216 is a tradename and product of The McIntyre Group, Ltd., University Park, Ill. Its INCI CTFA name is RICINOLEAMIDOPROPYL DIMETHYLAMINE LACTATE. The materials were mixed until a high solids emulsion was obtained. The high solids emulsion was diluted to 90% silicone solids. 0.25 g of the platinum complex in Example II was added to crosslink (i.e., cure) the emulsion particles. 5.56 g of this latex was blended in a WHIP MIX laboratory mixer with 30.71 g of the D4 and D5 mixture in Example III. The resulting composition was a dry thick gel.

EXAMPLE VII

Anionic Surfactant

Platinum Added Prior to Emulsification

In a laboratory WHIP MIX mixer, 100 g of the vinyl endblocked PDMS in Example V, 0.43 g of the ≡Si—H fluid in Example II, and 0.25 g of the platinum complex in EXAMPLE II, were mixed together. To this mixture, 7.50 g of a 40% aqueous solution of the anionic surfactant BIO-TERGE AS-40 was added. BIO-TERGE AS-40 is a tradename and product of Stepan Company, Northfield, Ill. It is a sodium alpha olefin sulfonate. The materials were mixed until a high solids emulsion was obtained. The high solids emulsion was diluted to 90% silicone solids. 5.56 g of this latex was blended in a WHIP MIX laboratory mixer with 30.71 g of the D4 and D5 mixture in Example III. The resulting composition was a dry thick gel.

EXAMPLE VIII

Amphoteric Surfactant

In a WHIP MIX laboratory mixer, 125 g of the vinyl endblocked PDMS in Example V, and 0.54 g of the ≡Si—H fluid in Example II were mixed together. To this mixture, 7.5 g of a 50% aqueous solution of the amphoteric surfactant SCHERCOTAINE SCAB was added. SCHERCOTAINE SCAB is a tradename and product of Scher Chemicals, Inc., Clifton, N.J. Its INCI CTFA name is COCAMIDOPROPYL HYDROXY SULTAINE. The materials were mixed until a high solids emulsion was obtained. The high solids emulsion was diluted to 90% silicone solids. 0.25 g of the platinum complex in EXAMPLE II was added to crosslink the emulsion particles. 5.56 g of this latex was blended in a WHIP MIX laboratory mixer with 30.71 g of the D4 and D5 mixture in Example III. The resulting composition was a dry thick gel.

EXAMPLE IX

Mineral Oil as Fluid 5.56 g of the latex prepared in Example VII, and 11.67 g of mineral oil, were mixed together until a homogenous, thick, smooth, white paste was formed.

Other variations may be made in compounds, compositions, and methods described without departing from the essential features of our invention. The forms of our invention are exemplary and not limitations on its scope defined in the claims.

We claim:

1. A method of modifying the viscosity of a solvent, the method comprising (I) adding a silicone latex containing water and a plurality of cured crosslinked polysiloxane particles to a solvent after the particles have been cured and without removing the water from the cured particles in the latex; and (II) mixing the latex containing the water and the cured particles and the solvent together to thicken the solvent; the latex being prepared by a method comprising:

(A) mixing (i) 100 weight parts of a siloxane polymer having a viscosity of greater than 5,000 mPa.s but less than 500,000 mPa.s at 25° C., (ii) 0.5–10 weight parts of a surfactant, and (iii) 0.5–25 weight parts of water, (B) emulsifying the mixture into a gel phase having a siloxane polymer content of at least 80% by weight; (C) diluting the emulsion with further water to a siloxane polymer content of at least 75% by weight, (D) adding 0.00001–20 weight parts catalyst either before or after the emulsification, or before or after the dilution; (E) adding 0.1–20 weight parts crosslinker either before or after the emulsification, or before or after the dilution; or in place of adding (D) and (E), adding 1–5 weight parts self catalytic crosslinker either before or after the emulsification, or before or after the dilution.

2. A method according to claim 1 in which the latex has a solids content of siloxane polymer of at least 90 percent by weight.

3. A method according to claim 1 in which the siloxane polymer has the formula $X_{3-n}R_n$—YO—$(R^1_2SiO)_z$—Y—

$R_nX_{3-n}$ where n is 0, 1, 2 or 3; z is an integer from 500–5,000; X is hydrogen, a vinyl group, a hydroxyl group, a condensable or hydrolyzable group; Y is a silicon atom, the group $\equiv Si-(CH_2)_m-SiR^1_2-$, or the group $\equiv Si-(CH_2)_m-SiR^1_2OSiR^1_2(CH_2)m-SiR^1_2-$, where m is 1–8; R is selected from the group consisting of aliphatic alkyl, aminoalkyl, polyaminoalkyl, epoxyalkyl, alkenyl, and an aromatic group; and $R^1$ is selected from the group consisting of X, aliphatic alkyl, alkenyl, and an aromatic group.

4. A method according to claim 3 in which the siloxane polymer has at least two vinyl groups per molecule bonded to a silicon atom, the crosslinker having an average of at least two silicon-bonded hydrogen atoms and being a silicon hydride crosslinker present in an amount sufficient to provide at least one hydrogen atom for each vinyl group in the siloxane polymer, and the catalyst is a noble metal catalyst.

5. A method according to claim 1 in which the self catalyzing crosslinker has at least one catalytic leaving group selected from the group consisting of acetoxy, amide, acetamide, aminoxy, and oxime.

6. A method according to claim 5 in which the self catalyzing crosslinker is a compound of the formula

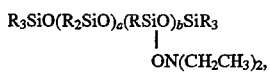
$$R_3SiO(R_2SiO)_a(RSiO)_bSiR_3$$
$$|$$
$$ON(CH_2CH_3)_2,$$

where R is the same or a different alkyl group of 1–8 carbon atoms; a is zero or a positive integer, and b is greater than two.

7. A method according to claim 1 in which the surfactant is selected from the group consisting of nonionic surfactants, cationic surfactants, anionic surfactants, amphoteric surfactants, and mixtures thereof.

8. A method according to claim 1 in which the solvent is selected from the group consisting of aromatic hydrocarbons, aliphatic hydrocarbons, alcohols, aldehydes, ketones, amines, esters, ethers, glycols, glycol ethers, alkyl halides, aromatic halides, petroleum hydrocarbons, lubricating oils, fatty oils, organic polysiloxanes, functional polysiloxanes, volatile methyl siloxanes, and mixtures thereof.

9. A latex thickened solvent composition prepared according to the method described in claim 1.

10. A latex thickened solvent composition according to claim 9 containing 5–40 percent by weight of the silicone latex and 60–95 percent by weight of the solvent.

11. A personal care product containing the latex thickened solvent composition of claim 9 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, shaving soaps, shaving lathers, hair shampoos, hair conditioners, hair sprays, mousses, permanents, depilatories, cuticle coats, make-ups, color cosmetics, foundations, blushes, lipsticks, eyeliners, mascaras, oil removers, cosmetic removers, delivery systems for oil and water soluble substances, and powders; including products in the form of sticks, gels, lotions, aerosols, and roll-ons.

12. A method of treating hair or skin comprising applying to the hair or skin a composition containing the latex thickened solvent composition of claim 9.

13. A product containing the latex thickened solvent composition of claim 9 and a material selected from the group consisting of crosslinked silicone rubber particles, pharmaceuticals, biocides, herbicides, pesticides, water, and water-soluble substances.

14. A method of modifying rheological, physical, or energy absorbing properties, of silicone or organic phases selected from the group consisting of sealants, paints, coatings, greases, adhesives, antifoams, and potting compounds, comprising incorporating therein the latex thickened solvent composition of claim 9 containing crosslinked silicone rubber particles.

15. A method of filling or insulating an electrical cable comprising incorporating therein the latex thickened solvent composition of claim 9.

16. A method of stabilizing in-ground soil or water barriers comprising incorporating into soil the latex thickened solvent composition of claim 9.

* * * * *